United States Patent [19]

Kharasch

[11] 3,982,999

[45] Sept. 28, 1976

[54] COMPLEXING CRESOLASE WITH COPPER CHELATING AGENTS

[76] Inventor: Jerome A. Kharasch, 6300 W. Touhy Ave., Niles, Ill. 60648

[22] Filed: July 26, 1974

[21] Appl. No.: 492,198

[52] U.S. Cl. ............................ 195/63; 195/68; 424/94; 424/DIG. 6
[51] Int. Cl.² ........................................ C07G 7/02
[58] Field of Search ............... 195/63, 68; 424/94, 424/DIG. 6

[56] References Cited
UNITED STATES PATENTS

| | | | |
|---|---|---|---|
| 2,956,929 | 10/1960 | Cohen et al. | 195/68 |
| 2,958,632 | 11/1960 | Schwarz et al. | 195/68 |
| 3,413,198 | 11/1968 | Deutsch | 195/63 X |

OTHER PUBLICATIONS

Hawley, G. G., The Condensed Chemical Dictionary, Van Nostrand Reinhold Co., N.Y., 1971 (p. 457).

Dawson, et al., Plant Tyrosinase (Polyphenol Oxidase), Methods in Enzymology, Academic Press Inc., N.Y., vol. II, 1955, (pp. 817–819).

*Primary Examiner*—David M. Naff
*Attorney, Agent, or Firm*—Burmeister, York, Palmatier, Hamby & Jones

[57] ABSTRACT

Complexes of Cresolase and copper chelating agents are used for inhibiting L1210 mouse leukemia. Particularly effective complexes are the chelates of cresolase with 8-hydroxyquinoline, $\alpha,\alpha$ dipyridyl, and hydroquinone. Tyrosinase obtained from the brown (Type I) common edible mushroom is a suitable source of cresolase. The cresolase active tyrosinase may then be reacted with copper chelating agent to produce the complex.

8 Claims, No Drawings

COMPLEXING CRESOLASE WITH COPPER CHELATING AGENTS

BACKGROUND OF THE INVENTION

The invention relates to complexing cresolase with copper chelating agents and includes the said complexes and a method for their preparation. It also includes a method of inhibiting L 1210 mouse leukemia using said complexes.

The tyrosinase gene is expressed only in mesenchymal melanocytes, functioning in mammals as dopa oxidase or catecholase. In other germ layers, tyrosinase exists at ribosomal membrane sites in blocked form, capable of release under conditions of tissue dissociation. This blocked tyrosinase (hereinafter called TYBLOC) functions as cresolase.

My theory of "binary sequencing" operationally defines TYBLOC by virtue of its effect on proline hydroxylase, as inhibitory to mesenchymal stem cell $\alpha$, $\alpha$ or non-differential division. TYBLOC therefore herein represents a naturally-occuring regulatory molecule which serves as the first line of defense of mesenchymal mitotic activity.

Such mitotic inhibition is imitated by complexes of cresolase-active tyrosinase and copper chelating agents. Raw material is brown (Type I) common edible mushroom. A production protocol for this TYBLOC complex is detailed herein.

The theory of binary sequencing began with the observation that cancer and mesenchyme are operationally equivalent. A subsequent article classified mesenchyme as the identity element of the mathematical group $S_3$. TYBLOC was found to satisfy the mathematical requirements for $Z_2$ of the group $S_3$ and its mode of action detailed.

Theoretically TYBLOC has the following functions:
1. as a frameshift doubler of quanine-cytosine residues in procollagen.
2. as a block to $\alpha,\alpha$ stem cell non-differential division.

The latter action is of interest, insofar as anti-carcinogenic activity is concerned. Its proposed mechanism is as follows:

TYBLOC complex is a blood-borne membrane-specific cresolase isoenzyme which carries a copper chelator to proline hydroxylase at the microsomes. Both tyrosinase and proline hydroxylase are copper-containing enzymes synthesized at ribosomal sites.

Proline bydroxylase, characteristic only of mechenchyme, was proposed as the cell-divisional initiator protein. By sharing the copper chelator of the TYBLOC complex, the action of proline in electronic oxidation is curbed, effectively switching off cell division. The balanced steady-state between differential and non-differential cell division is thereby maintained, and the switched-off cell differentiates.

On this view based entirely of applicant's theory and tests on mouse leukemia cancer represents a biochemical lesion in TYBLOC from "whatever" cause. Intravascular administration of TYBLOC complex serves as effective replacement therapy.

In electronic terms, TYBLOC represents a "load" upon current generated by the electronic oxidation activity of proline hydroxylase, a proposed enzymatic cell-divisional "trigger". A break in the TYBLOC according to applicant's theory leads to cancer by creating an electrical "short" in the proline hydroxylase oxidative system. Current diversion into this oxidative and mitotic pathway according to applicant's theory and tests on mouse leukemia results in cancer, whereby the steady-state between differential and non-differential cell division is distorted.

While I believe the above disclosed theory and mechanism are correct, it will be understood that my invention is not limited thereby.

EMPIRICAL OBSERVATIONS

The mechanism of TYBLOC action and theory of carcinogenesis detailed above clarifies some heretofore unexplained empirical observations:

1. The significance of tyrosinase localization in the outer surface of smooth-surface membranes has been unexplored. The $T_3$ fraction, in particular, is associated with ribosomes. Moreover, small amounts of cresolase activity has been found, both in normal mammalian melanocytes and melanoma. Only the melanosome-bound fraction was capable of catecholase activity, while the smooth membrane fraction, with high specific activity of tyrosinase, was incapable of incorporating dopa into melanin. The latter fraction might correspond to TYBLOC, where cresolase activity predominates.

2. The concept of a biochemical "break" in the TYBLOC molecule as carcinogenic clarifies both the paradoxical increase of cresolase-active tyrosinase in melanotic melanoma and localization of tyrosinase inhibitors in amelanotic melanoma.

3. Tyrosinase inhibitors which exhibit copper chelation have not been utilized as anti-leukemia agents, although radio-sensitization by halo-pyrimidines might function in this manner. BUDR and IUDR, in particular, are thought to act as radio-sensitizers by replacing DNA thymine. Any copper-chelation to proline hydroxylase would be minimized because the compound is not delivered to ribosomal sites by a tyrosinase carrier of cresolase activity.

CHEMICAL ASPECTS OF TYROSINASE

Tyrosinase catalyzes the oxidation of O-dihydric phenols such as catachol, pyrogallol, 3,4-dihydroxyphenylalanine, caffeic acid, protocatechuic acid, adrenaline, etc., but has no direct action on resorcinol, hydroquinone, or ascorbic acid. The latter two compounds could be oxidized indirectly, however, by adding a small amount of catechol to the system. Monohydric phenols such as phenol and p-cresol are oxidized only relatively slowly after a lag period. Tyrosine is oxidized directly, without any evidence of a lag period, but at a rate calculated about 1100 times slower than catechol. the latter is oxidized most rapidly of all substrates. The enzyme activity was inhibited by agents which chemically combine with copper, such as cyanide, diethyldithiocarbamate, salicylaldoxime, and carbon monoxide. He postulated that in its reaction with catechol, the enzyme copper is reduced to the cuprous state, which in turn is re-oxidized by molecular oxidation:

1. Two-stage reaction.

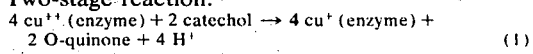

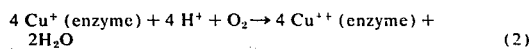

It is practice to refer to purified enzyme preparations as possessing marked activity toward catechol (catecholase activity) and little activity toward p-cresol (cresolase activity). It is now recognized that hydroquinone acts as an inhibitor, and all catecholase activity measurements made on a catechol-hydroquinone substrate mixture are considerably lower than those made on catechol directly.

The hydroxylation of tyrosine to dopa is the initial reaction in the biosynthesis of melanin catalyzed by tyrosinases, as shown in the equation below. ($AH_2$ represents an electron donor.)

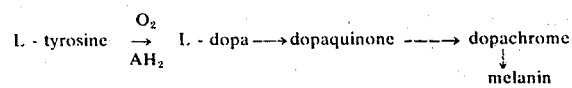

It is well recognized that enzyme solutions vary greatly in stability, and that many factors such as enzyme concentration, enzyme purity, pH, temperature, micro-organisms, foreign ions, etc., greatly influence the stability of enzyme solutions. These factors apply to TYBLOC. Sometimes enzymes are more stable in the dry form, but frequently the stability properties of the dried enzyme depend on the degree of purification affectd before the drying operation. In general, it can be stated that the stability of tyrosinase increases with purification, but it must be kept in mind that the concentration of the enzyme solution is important in this respect. Purified tyrosinase solutions, and TYBLOC solutions, that contain in excess of about 1 mg of enzyme protein per ml of solution, generally show little loss of activity over a period of several months if they are buffered to about pH 7, inoculated with a few drops of toluene (prevents growth of micro-organisms), and stored at refrigerator temperatures. The same enzymes however, when highly diluted for activity measurements, may exhibit a significant loss in activity in 15 or 20 minutes even though the temperature of the diluted enzyme is maintained at 0° – 5°C. The process, which is probably a dissociation or unfolding of the enzyme protein into less active forms, is considerably more rapid at room temperature.

The monophenolase (Cresolase) activity of the enzyme is less stable than the catecholase activity, as a general rule. Conditions known to result in protein denaturation, such as the application of heat (60°C) for a short period, or vigorous shaking of the protein solution in air for several hours, have been reported not only to seriously inactivate the enzyme, but also to cause significant increase in the ratio of catecholase to cresolase activity. As pointed out earlier, tyrosinase is made inactive by any agent which combines irreversibly with copper, or any condition that removes copper from the enzyme protein, such as dialysis at low pH.

One of the most striking characteristics of the enzymatic oxidation of catechol, as catalyzed by purified catalase preparations of tyrosinase, is the pronounced inactivation or destruction of the enzyme that occcurs during the course of the reaction. The inactivation is not due to any products known to be formed during the oxidation of catechol, but ocurs at the time the catechol is oxidized.

It is generally agreed that for an enzyme to catalyze a reaction, it must first combine with the substrate. In this way, tyrosinase is assumed to combine with phenolic bodies to form phenol-enzyme complexes.

TYROSINASE INHIBITION

It is speculated that the mechanism for the conversion of tyrosinase to TYBLOC is through a process of competitive inhibition, a reversible process. Competitive inhibition of an enzyme depends on the lack of absolute specificity of the chemical reactivity on the active site of the enzyme. The active site combines more or less loosely with the inhibitor, which is very possibly structurally related to the substrate, thus preventing access of the substrate to the enzyme surface. The degree of inhibition is dependent on the ratio substrate/inhibitor; sufficiently large concentrations of the substrate are able to displace the inhibitor completely from the enzyme.

The physical properties of TYBLOC are largely similar to tyrosinse. Tyrosinase behaves like a water soluble protein. It is very sensitive to elevated temperatures and low pH, and all operations must be carried out above pH 5 and in the vicinity of room temperature or lower to guard against denaturation.

Although many compounds inhibit tyrosinase, the theory as detailed demands inhibition by copper chelation to be utilized. Specifically, the chelators inhibiting tyrosinase must also chelate proline hydroxylase.

PROLINE HYDROXYLASE INHIBITION

The hydroxylation of proline is a non-specific hydroxylation by free radicals. It is possible to decrease the hydroxylation of proline in vitro by iron- and copper-chelating agents which prevent the release of electrons from metals and thus the formation of free radicals. Such $Fe^{2+}$ and $Cu^{2+}$ chelators are exemplified by $\alpha,\alpha'$-dipyridyl and 8-hydroxyquinoline.

A NATURALLY-OCCURING TYROSINASE INHIBITOR

Tyrosinase inhibitor found in amelanotic and melanotic melanoma exhibits the following properties:
1. heat stable
2. dialysable
3. exhibits no sulfhydryl properties
4. substantially inactivated by U.V. irradiation.

This study left open such quinone ring compounds as 8-hydroxyquinoline, hydroquinone, quinhydrone, pyrogallol and their derivatives.

Hydroquinone is the most promising candidate as a naturally occuring inhibitor, since it is a reduction product of coenzyme Q.

TYROSINASE PREPARATIONS

The raw material for the TYBLOC complex of this invention is mushroom tyrosinase, obtained from brown edible mushrooms of high cresolase activity. High cresolase preparations (CAT:CRES=1–10) are dark in color and possess low catecholase activity. Intermediate preparations (CAT:CRES=11–40) are less colored, while colorless preparations (CAT:CRES>40) have 4,000 CAT. units/mg.

Since tyrosinase preparations show polydispersity, several tyrosinase isoenzymes exist. The membrane-specific fraction exists only in the highest cresolase-active preparations. Such cresolase preparations are more unstable than those of high catecholase activity. They must be used in fresh stock solutions and not be shaken or heated to 60°C.

SUMMARY

In accordance with this invention a complex of cresolase and a copper chelating agent is administered to an animal having L 1210 mouse leukemia, in an amount sufficient to inhibit the growth of leukemia cells but not in greater amount than the animal can tolerate without undue harmful effect. The effective useful dosage varies with the type of chelating agent bound to the cresolase, the body weight of the animal and the type of animal. Such amounts can readily be determined by anyone skilled in the art.

The essence of the invention is the use of cresolase as a piggy-back carrier for copper chelators or ligand compounds especially ring ligand compounds in the treatment of L 1210 mouse leukemia.

Positive results are obtained in L1210 leukemic cultures and L1210 leukemic mice.

Particularly satisfactory results are obtained with the chelate complexes formed by reacting cresolase with $\alpha,\alpha$ dipyridyl, hydroquinone and 8-hydroxyquinoline, (cresolase-8-hydroxyquinoline).

The cresolase complex is administered dissolved in a sterile aqueous solution by parenteral injection as for example intraveneous or intraperitoneal injection.

Tyrosinase obtained from the brown (Type I) common edible mushroom is a suitable source of cresolase. The cresolase active tyrosinase obtained from such mushrooms may then be reacted with a copper chelating agent to produce the complex. Also substantially pure cresolase may be reacted with the copper chelating agent to produce a cresolase complex. The cresolase which is reacted may contain therapeutic non-toxic materials in addition to the cresolase. When cresolase active tyrosinase is used to produce the complexes the tyrosinase should contain a substantial amount of the cresolase, for example at least 10% of the oxidative activity should be cresolase activity and preferably the principal oxidative activity should be cresolase with a minor amount of catecholase activity being present.

The following experimental tests utilized 8-hydroxyquinoline as the metal chelator for cresolase. However, any derivitives of 8-hydroxyquinoline and related analogues are metal chelating agents and form anti-leukemia agents with cresolase and cresolase active tyrosinase. These chelating agents include 8-mercaptoquinoline, 7-chloro-8-hydroxyquinoline, 2-methyloxine, 4-azo-oxine, 4-hydroxyacridine, 6-hydroxy-m-phenantholine, 3,6-benzo-oxine, 8-methoxyquinoline, and 8-hydroxyquinoline-5-sulfonic acid.

In addition to oxine compounds other chelating agents which have been used for the treatment of animals and particularly those which have been used for leukemia treatment are of increased effectiveness when bound to cresolase either alone or as present in tyrosinase containing a substantial amount of cresolase.

Three such compounds are $\alpha,\alpha'$ dipyridyl, quinone, and hydroquinone (14 dihydroxybenzene). The production protocols are identical except for the chelator utilized. In the case of hydroquinone, however, solid catechol must be added to initiate the reaction.

All of these compounds as well s the 8-hydroxyquinoline bind to the copper of the cresolase and are carried by the cresolase to the site of the leukemia cells.

In obtaining a suitable cresolase complex toxic impurities are removed from the complex by such means as certrifuging, filtering and dialysis. Free chelator should also be removed from the complex so that when a sterile aqueous solution is made it does not have any substantial amount of free chelator present with the complex.

In accordance with one embodiment of this invention cresolase such as that obtained from brown mushrooms is mixed in aqueous solution with 8-hydroxyquinoline to form a protein complex of cresolase and chelator. A minor amount of the complex of catecholase and chelator may also be present, since this is sometimes found in small amount even in brown mushrooms.

Foreign solid impurities are removed from the aqueous solution of protein complex such as for example by centrifuging or filtering, and the solution is preferably dialyzed to dryness to obtain the solid complex. This solid complex is redissolved in aqueous solution, then filtered preferably by injecting through a millipore filter into a sterilized container. The solution in the container is capped and kept under refrigeration until ready for injection use. The solution may also be put in sterile ampules containing 500 mg. in 10 ml. for intraveneous injection. A suitable dose for average-human risk patients is 15 mg/kg daily for 5 days. Larger doses may be used in single injections of for example lg/kg. The injections may be continued for example for two weeks or until a remission occurs as evidenced by a return to normal bone marrow. If neither remission nor undue toxicity is encountered, variable lessened may be utilized or the dosages may be lesened depending upon the patient and his reaction.

DESCRIPTION OF THE PREFERRED EMBODIMENTS

Preparation of Complex of Cresolase With 8-Hydroxyquinoline

1. Dissolve 100.0 mg. (~1200 units/mg) of Grade I Mushroom Tyrosinase consisting mainly of cresolase activity in 100 ml 0.1 M Phosphate buffer, pH 6.8 (1200 units/ml.)
2. Determine activity of buffered cresolase active composition utilizing Sigma Tyrosine fluorimetric assay.
3. Label 3 beakers, No. 1, No. 2, No. 3.
   a. In beaker No. 1 add 25 ml. buffered cresolase plus 36.3 mg 8-Hydroxyquinoline, $10^{-2}$ M.
   b. In beaker No. 2 add 25 ml. buffered cresolase composition plus 3.63 mg 8-Hydroxyquinoline, $10^{-3}$ M.
   c. In beaker No. 3 add 25 ml. buffered cresolase composition plus 0.363 mg 8-Hydroxyquinoline,, $10^{-4}$ M.

Note: Determine final pH of each of above.

4. Incubate the contents of beakers 1, 2 and 3 for one (1) hour at 25° C with continuous mixing (magnetic stirrer).
5. Transfer contents of beakers 1, 2, and 3 to 50 ml. centrifuge tubes and resume incubation for an additional 2hours at 37° C.
6. Centrifuge at 1500 rpm.
7. Place each centrifugugate in a cellulose casing and dialyze against PVP (under refrigeration) to dryness.
8. Re-dissolve the protein complex (cresolase active-8-Hydroxyquinoline) in 25 ml. 0.1 M phosphate buffer, pH 6.8.
9. Determine the remaining activity of the cuffered Tyrosinase-8-Hydroxyquinoline composition for each dialysate to ascertin optimum Molar concentration of 8-hydroxyquinoline for inctivation of cresolase and any minor amount of catechlolase present.

Sterilization Procedure:

A. Place cresolase complex in a 50 ml. syringe; insert at Millipore (Millex) Disposable Filter Unit on end of syringe.

b. Inject solution comprising cresolase-8-hydroxyquinoline complex thru Millipore filter into a previously sterilized container. Cap and refrigerate.

EXPERIMENTAL RESULTS

Note: Stock solutions of tyrosinase consisted of Grade III mushroom tyrosinase. Data adjusted to cresolase Grade I.

A. SUBJECT: Effect of 8-hydroxyquinoline on Tyrosinase Activity"

TABLE I

| 8-Hydroxyquinoline Concentration[b] ($\mu$g/ml) | Reaction Rate ($\Delta$ OD/Min) | Inhibition (%) |
|---|---|---|
| 0 (Control) | 0.0433 | 0 |
| 10 | 0.0353 | 18.4 |
| 50 | 0.0160 | 63.0 |
| 200 | 0.0007 | 98.4 |

[b]Stock solutions of 8-hydroxyquinoline can be prepared using ethanol to give a concentration of 1 mg/ml in 4% ethanol.

"Tyrosinase (polyphenol oxidase) isolated from mushrooms and purchased from Sigma, St. Louis, Mo. The reaction was carried out in 2 quartz curvette containing 1 ml of phosphate buffer (0.5 M, pH 6.5) 1 ml of substrate (1 mM L-tyrosine in $H_2O$), 0.5 ml of solvent or drug, 0.5 ml $H_2O$ (for blank), 0.4 ml $H_2O$ and 0.1 ml of enzyme (0.5 mg/ml) for the reaction tube. The reaction was started by the addition of enzyme and the change of optical density ($\Delta$ O.D.) was determined at 1 min intervals. The enzyme rection was linear for at least 10 min (25°C ± 1).

B. SUBJECT: Tyrosinase 8-Hydroxyquinoline nd L1210 Leukemia Cells in Culture

The effects of tyrosinase (Ty) and 8-hydroxyquinoline (8-HQ) on L1210 leukemia cells in culture have been evaluated.

Initially, 8-HQ was found to be inhibitory to Ty (polyphenol oxidase Type III isolated from mushrooms, Sigma, St. Louis, Mo.) and the results are summarized in Table II. At 50 $\mu$ g/ml, a 63% inhibition was observed and the inhibition was dose-related.

8-HQ was also inhibitory to the growth of L1210 cells in culture. At 0.15 $\mu$g/ml, it inhibited cell growth over 60% and the inhibition was also dose-related. Surprisingly, tyrosinase was also found to be inhibitory to L1210 cell growth and a near complete inhibition was observed at 0.25 $\mu$g/ml (Table II). The latter phenomenon may be best explained by the depletion of tyrosine (and phenylalanine) from the medium as seen in Table III. In this experiment, we further investigated the effects of tyrosinase on L1210 cell growth with two media; 1) complete or regular medium and; 2) tyrosine-phenylalanine depleted medium. The results indicate that at 0.2 $\mu$g/ml, tyrosinase markedly inhibited cell growth (93.6 and 63.5% respectively in two experiments) when complete medium was used, but the inhibition was significantly reduced (39.8% and 0%, respectively) when tyrosine-phenylalanine depleted medium was used. With the depleted medium, cells do grow but at a much slower rate. These cells may adapt to the nutritional environment and require less tyrosine (and Phenylalanine) for their survival and hence their growth was less influenced by tyrosinase.

When 8 -HQ was preincubated with tyrosinase at room temperature for 30 min. prior to the addition of L1210 cells, the activity was lower than with either agent alone. This is due, on theoretical grounds, to the combination of two factors:

1. Depletion of tyrosine and phenylalanine by raw tyrosinase.

2. Combination of raw tyrosinase (cresolase fraction) with free natural blocking factors in culture producing TYBLOC in vitro. On theoretical grounds, leukemia is representd by a break in the TYBLOC complex, possibly due to conformational defects in body tyrosinase. Natural blocking factors (copper chelating agents) would be free-floating in tissue culture since no active metabolism of such factors takes place as in vivo.

TABLE II

Effect of 8-hydroxyquinoline and Tyrosinase on L1210 Cell Growth in Culture[a]

| | L1210 Cell Growth[b] | | | | | | | |
|---|---|---|---|---|---|---|---|---|
| | 8-Hydroxyquinoline ($\mu$g/ml) | | | | | | | |
| | 0 | | 0.1 | | 0.15 | | 0.2 | |
| Tyrosinase ($\mu$g/ml) | Growth | (%I) | Growth | (%I) | Growth | (%I) | Growth | (%I) |
| 0 | 147.9 | 0 | 126.8 | 14.3 | 56.4 | 61.9 | 7.4 | 95.0 |
| 0.125 | 85.8 | 42.0 | 163.4 | 0 | 105.7 | 28.5 | 14.7 | 90.1 |
| 0.25 | 0.8 | 99.5 | 19.4 | 86.9 | 17.2 | 88.4 | 1.5 | 99.0 |
| 0.5 | 0 | 100.0 | 0 | 100.0 | 0 | 100.0 | 0 | 100.0 |

[a]3-day cell growth inhibition assay.
[b]Cell Growth = (cell concentration day 3 - cell concentration day 0) × 10³; % Inhibition (%I) based on control growth of 147.9 × 10³ cells/ml.

It is emphasized that all results are run on Grade III white mushrooms, where catecholase/cresolase is > to cresolase Effectiveness is attributed, on previous theoretical grounds, tocresolase activity.

TABLE III

Effect of 8-Hydroxyquinoline and Tyrosinase on L1210 Cell Growth in Culture with Complete Medium and Tyrosine-phenylalamine Depleted Medium

| | Completed Medium | | Tyrosine and Phenylalamine Depleted Medium | |
|---|---|---|---|---|
| Treatment | Cell × 10³/ml[a] | Inhibition (%) | Cell × 10³/ml | Inhibition (%) |
| Control | 391.9 | | 102.5 | |
| 0.15 g/ml 8-Hydroxyquinoline | 344.5 | 12.1 | 55.8 | 45.6 |
| 0.1 g/ml Tyrosinase | 293.4 | 25.1 | 75.3 | 26.5 |
| 0.2 g/ml Tyrosinase | 25.1 | 93.6 | 61.7 | 39.8 |

TABLE III-continued
Effect of 8-Hydroxyquinoline and Tyrosinase on L1210 Cell Growth in Culture with Complete Medium and Tyrosine-phenylalamine Depleted Medium

| Treatment | | Completed Medium | | Tyrosine and Phenylalamine Depleted Medium | |
|---|---|---|---|---|---|
| | | Cell × $10^3$/ml[a] | Inhibition (%) | Cell × $10^3$/ml | Inhibition (%) |
| 0.15 g/ml 8-Hydroxyquinoline +0.1 g/ml Tyrosinase | | 180.3 | 54.1 | 57.2 | 44.1 |
| +0.2 g/ml Tyrosinase | | 117.2 | 70.1 | 51.4 | 49.9 |
| Control | | 358.5 | | 62.1 | |
| 0.15 g/ml 8-Hydroxyquinoline | | 280.2 | 21.8 | 29.7 | 52.2 |
| 0.1 g/ml Tyrosinase | | 370.8 | 0 | 90.7 | 0 |
| 0.2 g/ml Tyrosinase | | 130.7 | 63.5 | 77.6 | 0 |
| 0.15 g/ml 8-Hydroxyquinoline +0.1 g/ml Tyrosinase | | 126.5 | 64.4 | 32.9 | 46.8 |
| +0.2 g/ml Tyrosinase | | 128.2 | 64.2 | 39.6 | 36.2 |

[a]3-day cell growth inhibition assay.

C. SUBJECT: Antileukemia Activity of a Combination of 8-OH-quinoline and Tyrosinase The effect of a combination of 8-OH-quinoline and tyrosinase against L1210 mouse leukemia has been measured.

A preliminary toxicity study in non-leukemia, male $BDF_1$ mice indicated that the $LD_{50}$ of a single intraperitoneal (i.p.) dose of 8-OH-quinoline suspended in Klucel (0.3% hydroxy-propylcellulose) was ca 75 mg/kg. I.p. administered single doses of tyrosinase in 0.1M phosphate buffer (pH 6.5) up to 100 mg/kg resulted in no lethalities.

Male $BDF_1$ mice, initial weight ca 23g, were inoculated i.p. on Day 0 with $10^5$ L1210 cells per mouse. Treatment was initiated on Day 1 and continued through Day 9. Animals were weighed on days 1 and 5 to assess toxicity. Agents were prepared fresh daily as follows: 8-OH-quinoline (Eastman Chemical Co.) was dissolved in a small volume of absolute ethanol and diluted to the appropriate concentration with 0.1M sodium phosphate buffer, pH 6.5 (final ethanol concentration: 3%). Dilutions were made in buffer containing 3% ethanol. Tyrosinase[2] (Sigma Chemical Co., lot 121C-9530) was dissolved in buffer containing 3% ethanol. (Previous studies had shown that 3% ethanol had no effect on the activity of the enzyme) For the combination, 8-OH-quinoline was again dissolved in a small volume of ethanol, but diluted with 0.1M sodium phosphate buffer; pH6.5, containing tyrosinase in the appropriate concentration. Dilutions were made in buffer containing both 3% ethanol and tyrosinase so that both ethanol and tyrosinase concentrations remained constant as the 8-OH-quinoline concentration decreased. The combination was "incubated" at room temperature for 30 minutes before administration. The radio of enzyme to substrate administered in the combination was varied from 1:1 to 1:.125.

Actual doses administered and results comprise Table IV. Results are expressed as the ratio (T/C) of the test group mean day of death to control group mean day of death.

TABLE IV
Antitumor Activity Of A Combination Of 8-OH-quinoline And Tyrosinase

| Agent | mg/kg/day | Mean day of Death (I.S.D.) | T/C* | Day 1-5 Weight Change,gm/mouse |
|---|---|---|---|---|
| 8-OH-quinoline | 20 | 9.5 ± 0.8 | .97 | +1.0 |
| | 10 | 9.5 ± 0.4 | .97 | +1.0 |
| | 5 | 9.0 ± 0.6 | .92 | +1.4 |
| | 2.5 | 9.3 ± 0.8 | .95 | −0.3 |
| 8-OH-quinoline/ tyrosinase | 20/20 | 9.8 ± 0.4 | 1.00 | +0.4 |
| | 10/20 | 11.7 ± 0.4 | 1.20 | +0.8 |
| | 5/20 | 12.2 ± 0.5 | 1.24 | +0.4 |
| | 2.5/20 | 12.4 ± 0.6 | 1.26 | +0.5 |
| Tyrosinase | 20 | 9.8 ± 0.7 | | +0.3 |
| Controls (uninjected) | | 9.8 ± 0.7 | | +1.3 |
| Controls (buffer) | | 9.5 ± 0.6 | | +1.5 |

*T/C's were calculated using the uninjected control group.
[1]6 mice 1 treatment group
[2]Catalogue No. 7755, polyphenoloxidase, from mushrooms, Grade III 3690 units/mg The complexes of cresolase with the copper chelators disclosed above are effective in non-lethal doses in the animals tested. It is understood, however, that the effective dose should be based upon the amount of cresolase activity present in the tyrosinase and for best results a composition consisting predominantly of the cresolase with a copper chelating agent such as 8-hydroxyquinoline, $\alpha,\alpha$ dipyridyl or hydroquinone is used in a pharmaceutical nontoxic carrier.

I claim:

1. A complex of cresolase and a copper chelating agent selected from the compounds consisting of 8-hydroxyquinoline, 8-mercaptoquinoline, 7-chloro-8-hydroxyquinoline, 2-methyl-oxine, 4-azo-oxine, 4-hydroxyacridine, 6-hydroxy-m-phenantholine, 3,6-benzo-oxine, 8-methoxyquinoline, 8-hydroxyquinoline-5-sulfonic acid and $\alpha,\alpha$ dipyridyl.

2. A complex in accordance with claim 1 in which the copper chelating agent is 8-hydroxyquinoline.

3. A complex of tyrosinase and a chelating agent selected from the group of compounds consisting of 8-hydroxyquinoline,, 8-mercaptoquinoline, 7-chloro-8-hydroxyquinoline, 2-methyl-oxine, 4-azo-oxine, 4-hydroxyacridine, 6-hydroxy-m-phenantholine, 3,6-benzo-oxine, 8-methoxyquinoline, 8-hydroxyquinoline-5-sulfonic acid and $\alpha,\alpha$ dipyridyl, in which at least 10 per cent of the oxidative acitivity of said tyrosinase is cresolase activity.

4. A complex in accordance with claim 3, in which the chelating agent is 8-hydroxyquinoline.

5. A method of making the complex of claim 1 which comprises mixing tyrosinase of the type present in brown edible mushrooms with a chelating agent selected from the group of compounds consisting of 8-hydroxyquinoline, 8-mercaptoquinoline, 7-chloro-8-hydroxyquinoline, 2-methyl-oxine, 4-azo-oxine, 4-hydroxyacridine, 6-hydroxy-m-phenantholine, 3,6-benzo-oxine, 8-methoxyquinoline, 8-hydroxyquinoline-5sulfonic acid and $\alpha,\alpha$ dipyridyl in aqueous solution to produce a composition consisting essentially of a complex of cresolase with one of said chelating agents in aqueous solution, separating solids from the solution and dialyzing the remaining solution to obtain the solid complex.

6. A method in accordance with claim 5 in which the tyrosinse is dissolved in an aqueous phosphate buffered solution at a pH of approximately 6.8.

7. A method in accordance with claim 5 in which the solid complex is dissolved in a phosphate buffered aqueous solution and filtered into a millipore filter into a sterilized container.

8. A method in accordance with claim 5 in which the brown mushroom tyrosinase is mixed with 8-hydroxyquinoline.

* * * * *